United States Patent
Rajhansa

(10) Patent No.: US 6,231,578 B1
(45) Date of Patent: May 15, 2001

(54) ULTRASONIC SNARE FOR EXCISING TISSUE

(75) Inventor: Dipak Rajhansa, Farfield, CT (US)

(73) Assignee: United States Surgical Corporation, Norwalk, CT (US)

( * ) Notice: Subject to any disclaimer, the term of this patent is extended or adjusted under 35 U.S.C. 154(b) by 0 days.

(21) Appl. No.: 09/365,686

(22) Filed: Aug. 2, 1999

Related U.S. Application Data

(60) Provisional application No. 60/095,420, filed on Aug. 5, 1998.

(51) Int. Cl.[7] ............................ A61B 17/32; A61B 10/00
(52) U.S. Cl. .............................................. 606/113; 606/46
(58) Field of Search ..................... 606/113, 46

(56) References Cited

U.S. PATENT DOCUMENTS

| | | |
|---|---|---|
| D. 362,504 | 9/1995 | Younker et al. . |
| 3,818,913 | 6/1974 | Wallach . |
| 3,862,630 | 1/1975 | Balamuth . |
| 3,990,452 | 11/1976 | Murry et al. . |
| 4,188,952 | 2/1980 | Loschilov et al. . |
| 4,271,371 | 6/1981 | Furuichi et al. . |
| 4,345,599 | 8/1982 | McCarrell . |
| 4,425,115 | 1/1984 | Wuchinich . |
| 4,445,063 | 4/1984 | Smith . |
| 4,587,958 | 5/1986 | Noguchi et al. . |
| 4,626,728 | 12/1986 | Flachenecker et al. . |
| 4,634,420 | 1/1987 | Spinosa et al. . |
| 4,763,667 | 8/1988 | Manzo . |
| 4,763,670 | 8/1988 | Manzo . |
| 4,827,911 | 5/1989 | Broadwin et al. . |
| 4,886,060 | 12/1989 | Wiksell . |
| 5,026,371 | 6/1991 | Rydell et al. . |
| 5,078,716 | 1/1992 | Doll . |
| 5,122,147 | 6/1992 | Sewell, Jr. . |
| 5,158,561 | 10/1992 | Rydell et al. . |
| 5,163,421 | 11/1992 | Bernstein et al. . |
| 5,171,314 | 12/1992 | Dulebohn . |
| 5,190,542 | 3/1993 | Nakao et al. . |
| 5,201,740 | 4/1993 | Nakao et al. . |
| 5,207,686 | 5/1993 | Dolgin . |
| 5,336,227 | 8/1994 | Nakao et al. . |
| 5,403,276 | 4/1995 | Schechter et al. . |
| 5,417,654 | 5/1995 | Kelman . |
| 5,447,510 | 9/1995 | Jensen . |
| 5,449,370 | 9/1995 | Vaitekunas . |
| 5,462,553 | 10/1995 | Dolgin . |
| 5,464,016 | 11/1995 | Nicholas et al. . |
| 5,480,379 | 1/1996 | La Rosa . |
| 5,486,182 | 1/1996 | Nakao et al. . |
| 5,573,530 * | 11/1996 | Fleury et al. ............... 606/113 |
| 5,613,973 * | 3/1997 | Jackson et al. ............ 606/113 |
| 5,630,837 | 5/1997 | Crowley . |
| 5,651,788 | 7/1997 | Fleischer et al. . |
| 5,674,235 | 10/1997 | Parisi . |
| 5,957,932 * | 9/1999 | Bates et al. ................ 606/113 |
| 5,989,264 * | 11/1999 | Wright ....................... 606/113 |

FOREIGN PATENT DOCUMENTS 1526-704  12/1989  (SU) .

\* cited by examiner

*Primary Examiner*—Paul J. Hirsch

(57) ABSTRACT

A surgical instrument for excising includes an endoscopic portion with an ultrasonically vibratable loop. The loop is positioned around the tissue and closed, whereupon ultrasonic energy is transmitted to the loop to cut and cauterize the body tissue. The apparatus and method described herein are particularly suitable for colonoscopic polypectomy procedures.

20 Claims, 5 Drawing Sheets

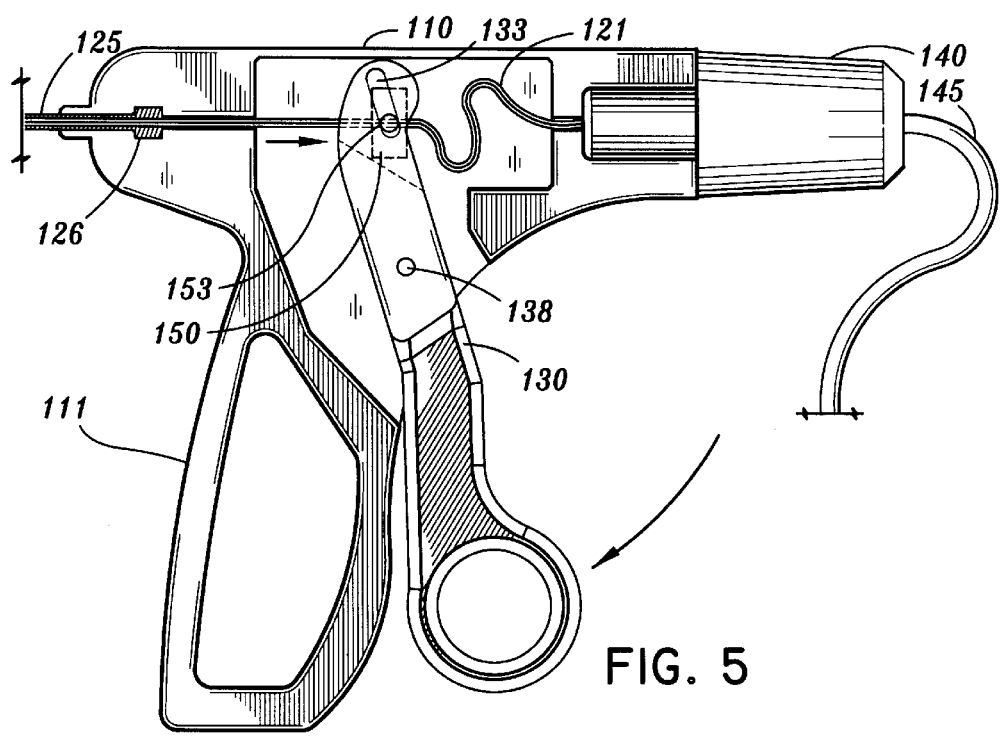
FIG. 5
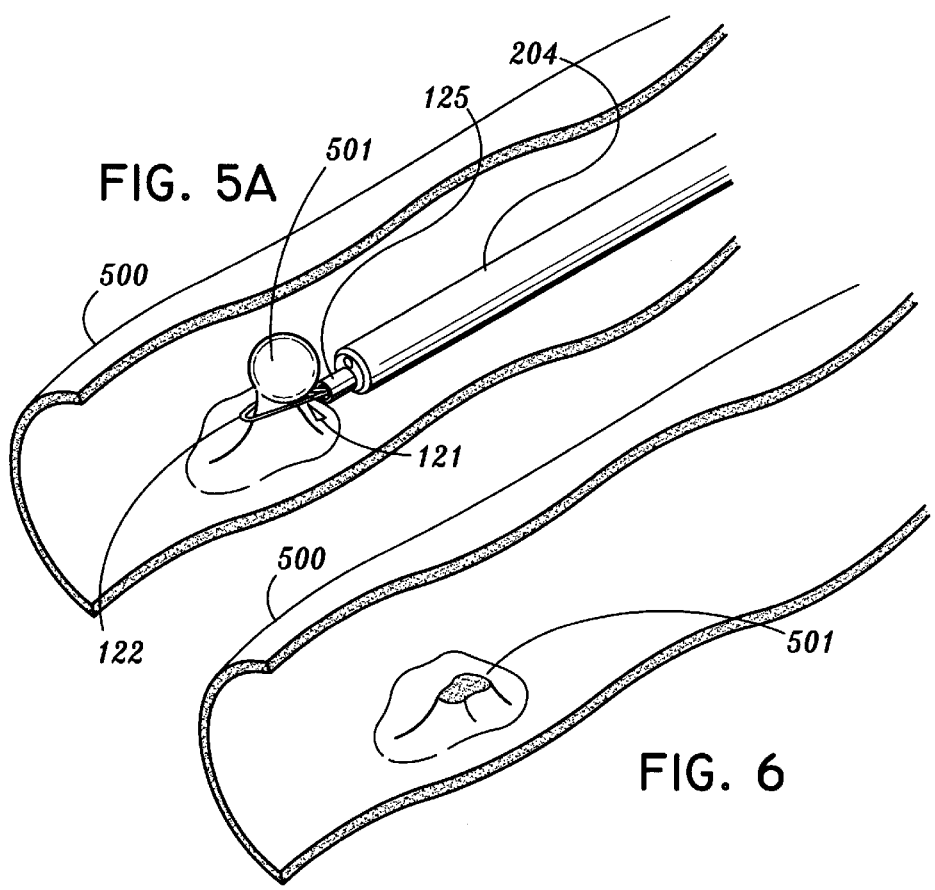
FIG. 5A
FIG. 6

ULTRASONIC SNARE FOR EXCISING TISSUE

This application claims the benefit of Provisional No. 60/095,420 filed Aug. 5, 1998.

BACKGROUND

1. Technical Field

The present disclosure relates to a surgical instrument assembly for use in excising body tissue from an internal body cavity, and more particularly to a snare device for removing polyps.

2. Background of Related Art

Colonoscopic polypectomy is a commonly used method for removing and optionally retrieving polyps from the colon. Such operations are performed so that the polyps can be examined by a pathologist for malignancy. Devices for such removal and retrieval of tissue are disclosed and described in U.S. Pat. Nos. 5,486,182, 5,336,227, 5,201,740 and 5,190,542, to Nakao et al.

Typically, a snare device is used which has a distal loop of wire which can be inserted into the colon and positioned around the base of the polyp. Thereafter, the loop is closed around the stalk of the polyp to sever the tissue.

One complication which can develop with simple mechanical excision of the polyp is excessive bleeding. In order to reduce the amount of bleeding that can result from severing the polyp from its stalk some surgical apparatus employ an electrocautery snare. The electrocautery device can be monopolar as disclosed for example in U.S. Pat. No. 5,158,561, or bipolar as disclosed for example in U.S. Pat. Nos. 5,026,371 and 4,905,691. Monopolar devices generally use radio frequency ("rf") current.

Nevertheless complications can occur during electrocautery polypectomy procedures. For example, colonic perforation can result from the electrocautery current travelling via blood vessels to the base of the polyp and the wall of the colon, from the current travelling through the head of the polyp to the opposite wall, and from the accidental contact of the active electrode with surrounding tissue. Also, unobserved damage can occur from microperforations of the bowel wall and from pooled body fluids which contact the electrified wire and carry the current along unintended pathways to locations outside the field of view.

There yet remains a need for a polypectomy snare which provides the advantage of tissue cutting and coagulation while avoiding the disadvantages of electrocautery current.

SUMMARY

A surgical instrument is provided herein for cutting body tissue. The instrument includes a housing, an endoscopic portion including an ultrasonically vibratable element at least partially extending from the housing, an actuator movably connected to the housing and fixedly attached to the ultrasonically vibratable element, and an ultrasonic transducer operatively connected to the ultrasonically vibratable element.

The ultrasonically vibratable element possesses a loop at a distal end, the loop being movable between an open configuration for the reception of the body tissue therethrough and a closed configuration. Movement of the actuator between a first position and second position effects corresponding movement of the loop between the open configuration and closed configuration.

Also provided herein is a method for surgically removing polyps by employing the surgical instrument described herein.

The surgical instrument described herein advantageously limits bleeding during polypectomy operations while providing a greater margin of safety to the patient.

BRIEF DESCRIPTION OF THE DRAWINGS

Various embodiments are described below with reference to the drawings wherein:

FIG. 5 is a sectional side view of the hand-held ultrasonic surgical instrument in a closed configuration;

FIG. 5A is a cutaway perspective view of the colon showing the closure of the snare loop around the base of the polyp; and FIG. 6 is a cutaway perspective view showing the colon with the polyp removed.

DETAILED DESCRIPTION OF PREFERRED EMBODIMENTS

The apparatus of the present disclosure is intended to snare body tissue and deliver ultrasonic energy to the snared tissue for the purpose of excising the tissue while limiting bleeding. The apparatus may be used in any minimally invasive surgical procedure where removal of tissue growths is desired, and it has particular application for the removal of polyps from the colon, although the apparatus is not limited to such application.

The apparatus is particularly intended to be used in conjunction with an endoscope such as a cystoscope, fiber scope, laparoscope, urethroscope or the like, to provide the scope with ultrasonic treatment capabilities. More specifically, the apparatus is at least partially insertable within the working channel of an endoscope which has been positioned in the body to access a targeted tissue area to treat the desired tissue.

Figure 1:
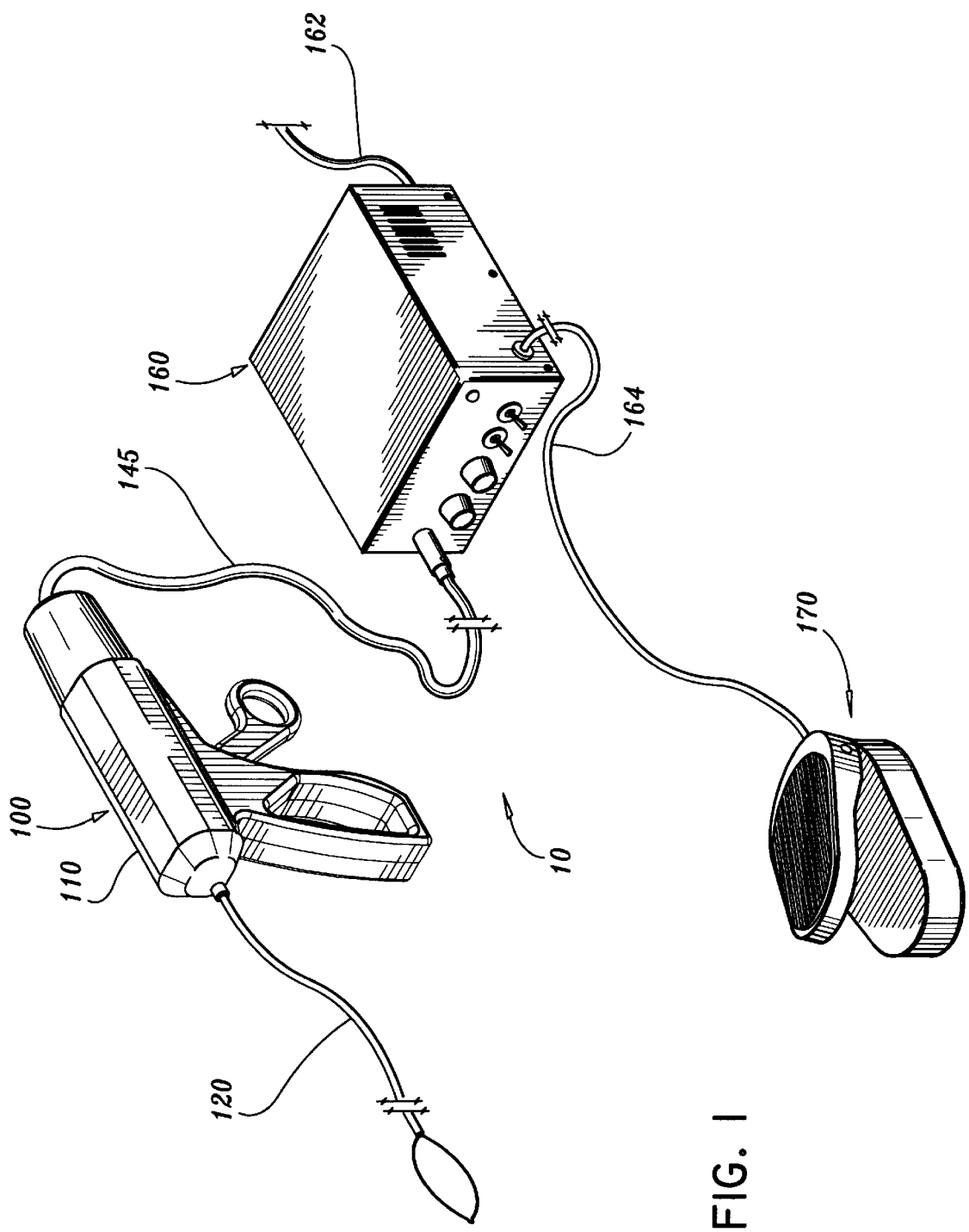
FIG. 1 is a perspective view of the ultrasonic system for excising body tissue.

Referring to FIG. 1, the ultrasonic system 10 for excising body tissue includes a hand-held ultrasonic surgical instrument 100 including a body portion 110 and an endoscopic snare portion 120. The ultrasonic system 10 further includes a control module 160, and optionally a pedal switch 170.

Figure 2:
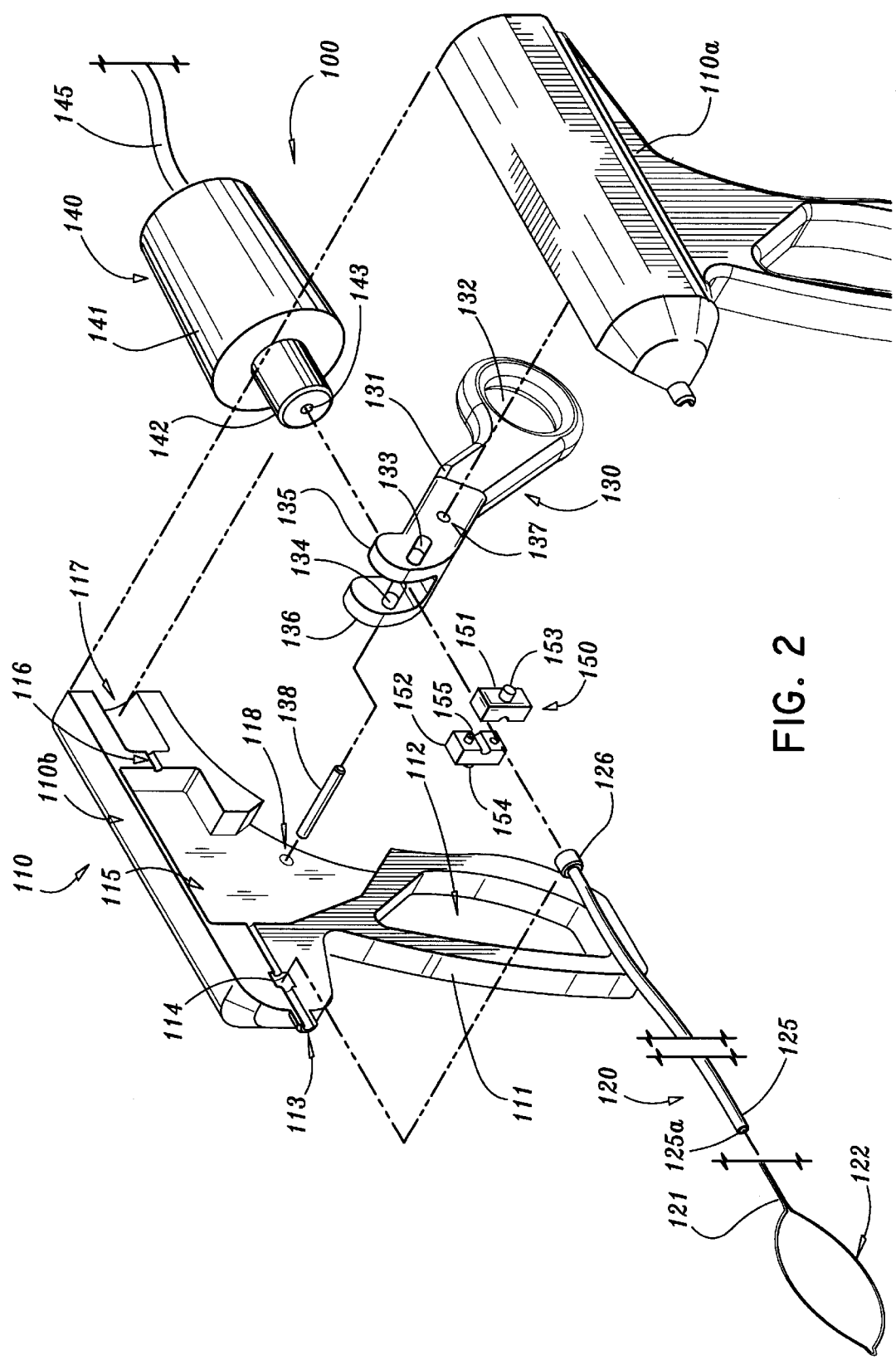
FIG. 2 is an exploded perspective view of the hand held ultrasonic surgical instrument including the ultrasonic snare.

Referring also now to FIG. 2, endoscopic portion 120 includes a flexible wire snare 121 terminating in a distal loop 122. Snare 121 extends through tubular outer sheath 125 having a cylindrical retainer 126 at the proximal end thereof. The snare wire is preferably fabricated from a biocompatible metal alloy such as stainless steel, titanium, and alloys of titanium, aluminum and vanadium, and may optionally be coated with an electrically insulative polymeric material such as polyimide. Snare 121 is slidably disposed within sheath 125 and is movable between a distal position wherein loop 122 is outside the distal edge 125a of sheath 125 and resiliently expanded to an open configuration, and a proximal position wherein loop 122 is at least partially withdrawn into outer sheath 125 and cammed by the distal edge 125a of sheath 125 into a closed configuration. Sheath 125 can be fabricated from a flexible plastic or metal alloy.

The endoscopic portion 120 is connected to the body portion 110. The left and right body halves 110a and 110b, respectively, can be fabricated from polymeric resin by any suitable method such as, for example, injection molding, and can be joined to form body portion 110 by solvent welding, adhesive bonding, heat welding or any other appropriate method. When joined, left and right body halves 110a and 110b define an axially extending distal channel 113 having a recess 114 configured and dimensioned for reception of retainer portion 126 of outer casing 125, an interior chamber 115, a proximal channel 116, and proximal cavity 117. Handle 111 of the body portion 110 includes a grip 112 for the user's fingers.

Clamp 150 includes left and right halves 151 and 152, respectively, each having a laterally extending boss 153 and 154, respectively. When joined, halves 151 and 152 define an axial channel 155 through which wire snare 121 is disposed. Clamp 150 frictionally engages and securely holds snare 121.

Trigger 130 is pivotally mounted to body portion 110 by means of a pin 138 which extends laterally through aperture 118 in the body portion and through aperture 137 in the trigger 130. The body 131 of the trigger is elongated and terminates at one end at ring portion 132 adapted to receive the finger of a user. At the end opposite ring 132, body 131 includes left and right projections 135 and 136, respectively, which are separated by a space into which clamp 150 is received. Projections 135 and 136 each include an elongated aperture 133 and 134 respectively, which are adapted to receive a respective one of bosses 153 and 154.

The ultrasonic transducer 140 includes a transducer unit 141 having a distal plug portion 142 which is adapted to engage and be received into proximal cavity 117 of the body portion 110. Optionally, the distal plug portion 142 can frictionally engage proximal cavity 117 or may alternatively be secured by, for example, a bayonet type mounting feature or screw-in type mounting. The ultrasonic transducer 140 includes a transducer horn actuated by one or more piezoelectric crystals. Snare wire 121 extends through opening 143 in the ultrasonic transducer 140 and is operatively connected to the transducer horn. The piezoelectric crystals are electrically connected to a control module 160 by means of a conductive cable 145. The control module 160 provides a regulated power supply to the ultrasonic transducer 140 and can optionally be actuated by a pedal switch 170 via cable 164. Cable 162 supplies power to the control module 160 from a standard electrical outlet. The ultrasonic transducer 140 causes linear oscillation of the wire snare 121 at frequencies above about 20 kHz, typically about 30 kHz to about 50 kHz. The ultrasonic oscillations of the wire snare generate shear waves which facilitate cutting of tissue by fragmenting cellular material.

The ultrasonic energy advantageously promotes clotting of blood. The high frequency shear waves induced by the ultrasonic vibrations cannot be supported by body tissue. Therefore, the energy of the shear waves is absorbed by the surrounding tissue and dissipated in the form of heat. This promotes fibrin formation and clotting of blood. Damage to underlying tissue is minimized because the shear waves do not travel far from the vicinity of the cutting site.

Figure 3:
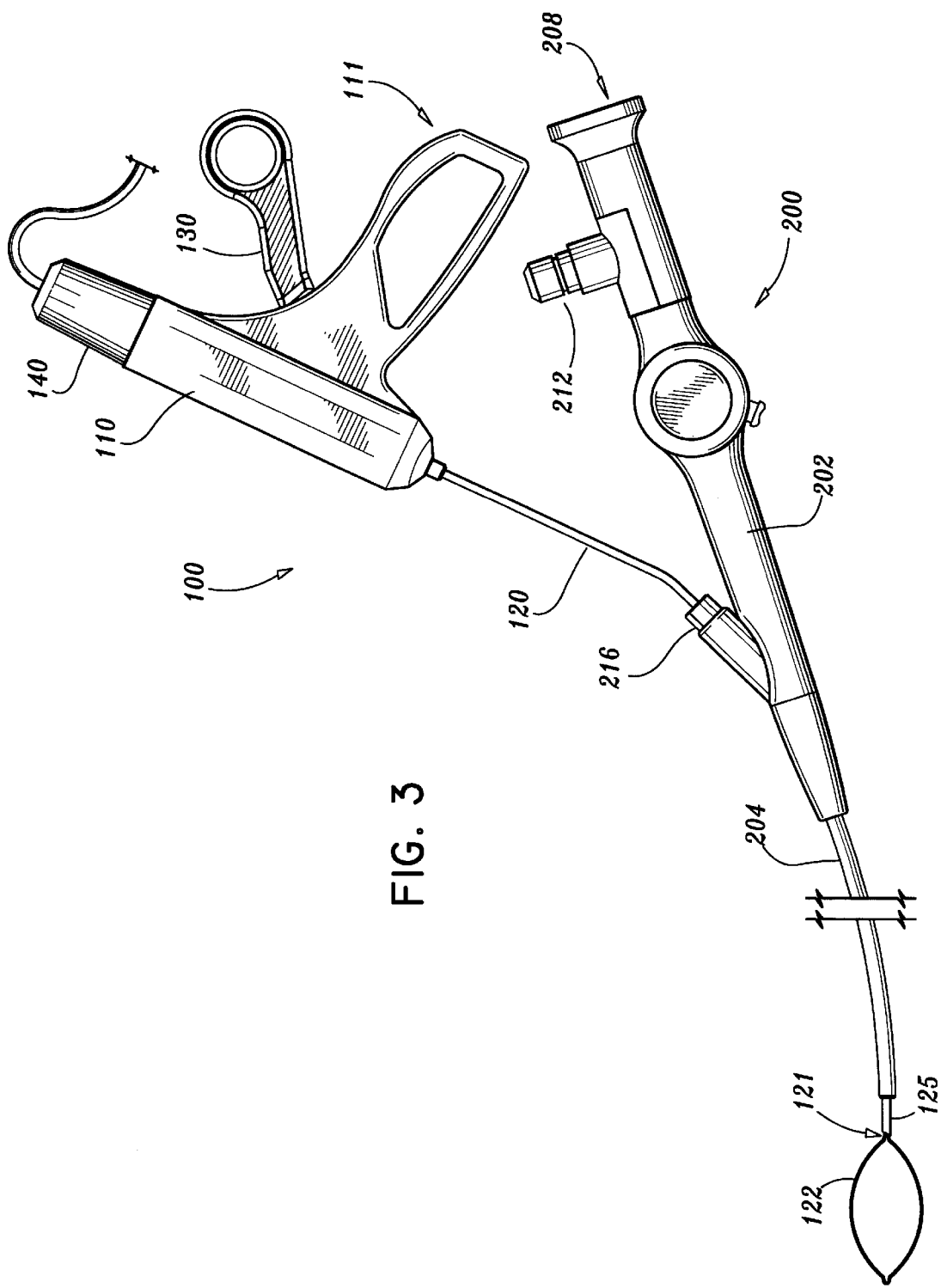
FIG. 3 is a side view illustrating the use of the apparatus in conjunction with a cannula assembly.

Referring now to FIG. 3, use of the ultrasonic snare assembly 100 in conjunction with an endoscope is shown. An endoscope suitable for use with the apparatus of the present disclosure is a cystoscope such as the ACN Cysto Nephroscope, which is available from Circon ACMI.

Cystoscope 200 includes handle 202 and a flexible elongated portion 204 connected to the handle 202 and extending distally therefrom. Cystoscope 200 incorporates an optical system to permit viewing of the tissue to be treated. The optical system preferably consists of flexible fiber optic bundles (not shown) which are accommodated within a longitudinal bore extending through the elongated portion 204 of the scope 200. The fiber optic bundles extend to eyepiece 208 where the surgeon can view the image transmitted by the optical system.

Cystoscope 200 also includes an illumination system which provides illuminating light to the targeted tissue area. The illumination system includes a plurality of optical fibers (not shown) which are accommodated within a plurality of longitudinal channels (not shown) of elongated portion 204 and extend within handle 202 where they terminate at illumination coupler 212. Illumination coupler 212 is connectable to a conventional light source as is known in the art. Cystoscope 200 further includes a working channel extending through flexible elongated portion 204 and terminating at channel port 216 of handle 202. The working channel is adapted to receive various surgical instrumentation through channel port 216 to permit the performance of surgical procedures at the distal end of the cystoscope 200.

In use the cystoscope flexible elongated portion 204 is inserted into the colon of the patient. The endoscopic portion 120 of the ultrasonic snare assembly 100 is inserted through channel port 216 of the cystoscope.

Figure 4:
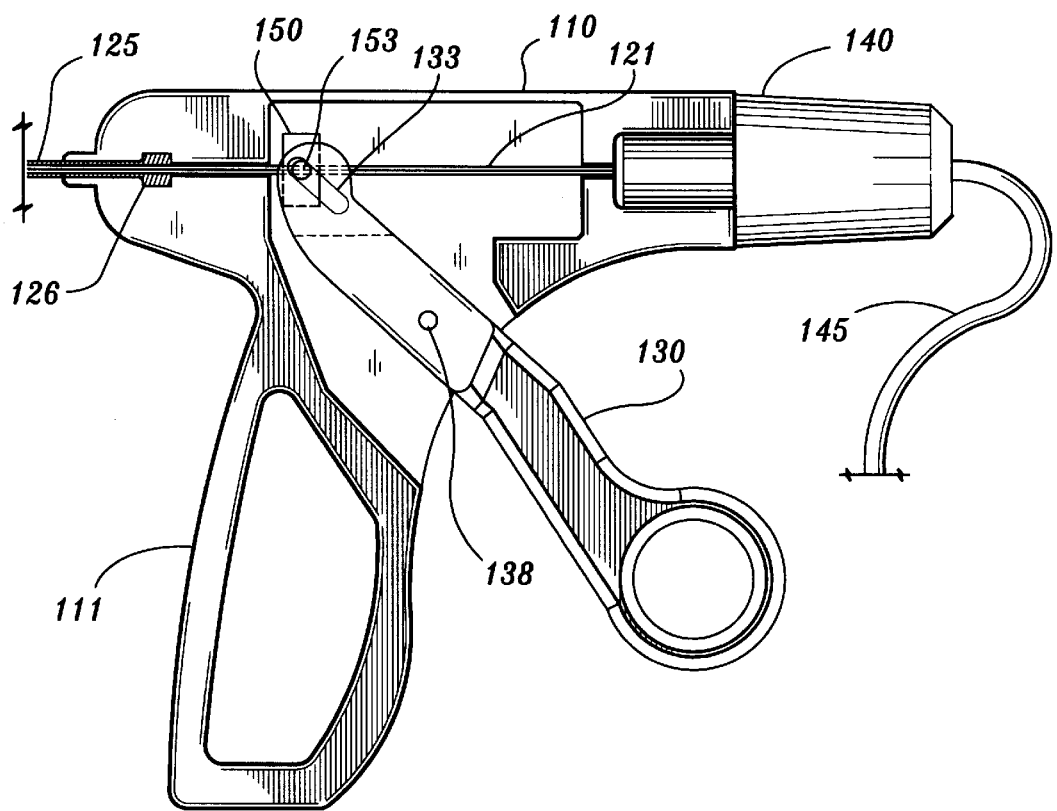
FIG. 4 is a cut-away side view of the hand-held ultrasonic surgical instrument in an initial configuration.
Figure 4A:
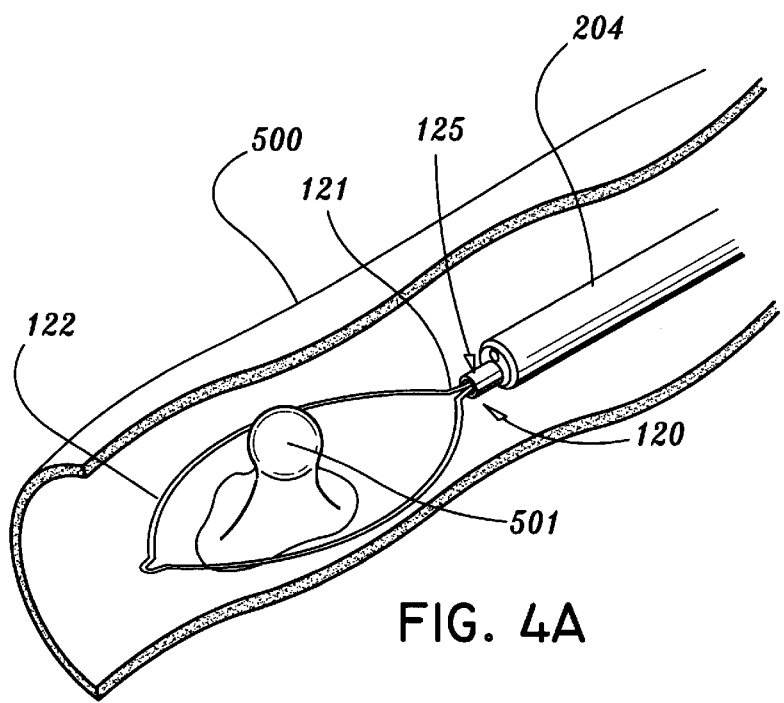
FIG. 4A is a cutaway perspective view of the colon showing the placement of the snare loop around a polyp.

Referring now to FIGS. 4 and 4A, the loop 122 is positioned around polyp 501 within the colon 500 of the patient. The ultrasonic surgical instrument 100 is initially in the configuration shown in FIG. 4. Clamp 150 and trigger 130 are in their respective initial positions.

Referring now to FIGS. 5 and 5A, the snare loop 122 is tightened around polyp 501 by pivoting trigger 130 clockwise (as shown), which pulls clamp 150 and the snare wire 121 proximally. The elongated configuration of slot 153 accommodates the arcuate motion of the upper end of trigger 130 by permitting the bosses 153 and 154 of clamp 150 to slide along the length of slot 133. This permits the clamp to be moved linearly. The user can then apply ultrasonic energy to the snare wire 121 to facilitate the cutting of the polyp. As shown in FIG. 6 after the main portion of the polyp is removed, there remains the base area of the polyp cut and cauterized by the ultrasonic snare. Ultrasonic cauterization limits the amount of bleeding while reducing the risk of unintended and perhaps unobserved damage to body tissue.

Although shown for removing polyps it should be understood that the ultrasonic instrument 100 could alternatively be used in other surgical procedures.

It will be understood that various modifications may be made to the modifications shown herein. For example, the body portion 110 can be fabricated from various metal alloys, as well as from various polymers such as acrylics, polycarbonates, and the like. Therefore, the above description should not be construed as limiting but merely as exemplifications of preferred embodiments. Those skilled in the art will envision other modifications within the scope and spirit of the claims appended hereto.

What is claimed is:

1. A surgical instrument for cutting body tissue comprising:
   a) a housing;
   b) an endoscopic portion including an ultrasonically vibratable element at least partially extending from the housing, the ultrasonically vibratable element possessing a loop at a distal end, the loop being movable between an open configuration for the reception of body tissue therethrough and a closed configuration;

c) an actuator movably connected to the housing and fixedly attached to the ultrasonically vibratable element, wherein movement of the actuator between a first position and a second position effects respective movement of the loop between the open configuration and the closed configuration; and d) an ultrasonic transducer operatively connected to the ultrasonically vibratable element.

2. The instrument of claim 1 wherein the ultrasonically vibratable element comprises a metal wire.

3. The instrument of claim 2 wherein the metal wire is fabricated from a material selected from the group consisting of stainless steel, titanium and alloys containing titanium, aluminum and vanadium.

4. The instrument of claim 1 wherein the endoscopic portion further includes a sheath and the ultrasonically vibratable element is slidably disposed within a bore of the sheath.

5. The instrument of claim 4 wherein the sheath includes a distal end and wherein, in the open configuration, the loop is outside the sheath, and in the closed configuration the loop is at least partially inside the bore of the sheath.

6. The instrument of claim 1 wherein the ultrasonically vibratable element is connected to a clamp.

7. The instrument of claim 6 wherein the clamp includes at least one laterally oriented projection.

8. The instrument of claim 7 wherein the actuator includes at least one slot through which the at least one laterally oriented projection of the clamp is disposed.

9. The instrument of claim 8 wherein the actuator is pivotally mounted to the housing.

10. The instrument of claim 9 wherein the slot is elongated.

11. The instrument of claim 1 wherein the ultrasonically vibratable element is at least partially coated with a polymeric material.

12. An ultrasonic system for excising body tissue comprising:

a) a housing;

b) an endoscopic portion distally extending from the housing, the endoscopic portion including a tubular sheath and an ultrasonically vibratable element slidably disposed through the tubular sheath, the ultrasonically vibratable element possessing a loop at a distal end, the loop being movable between an open configuration for the reception of tissue therethrough and a closed configuration;

c) an actuator movably connected to the housing and fixedly attached to the ultrasonically vibratable element wherein movement of the actuator between a first position and a second position effects respective movement of the loop between the open configuration and the closed configuration;

d) an ultrasonic transducer operatively connected to the ultrasonically vibratable element; and, e) a control module for providing regulated electrical power to the ultrasonic transducer.

13. The system of claim 12 further including a pedal switch for controlling the flow of electrical power from the control module to the ultrasonic transducer.

14. The system of claim 12 further including an endoscope having a channel through which the endoscopic portion is slidably disposed.

15. A method for surgically removing polyps comprising:

a) providing a surgical instrument for cutting body tissue which includes a housing, an endoscopic portion distally extending from the housing, the endoscopic portion having an ultrasonically vibratable element possessing a loop at a distal end, the loop being movable between an open configuration for the reception of body tissue therethrough and a closed configuration, and an ultrasonic transducer operatively connected to the ultrasonically vibratable element;

b) positioning the open configured loop around the polyp to be excised;

c) closing the loop; and d) applying ultrasonic power to the loop.

16. The method of claim 15 wherein the ultrasonic transducer operates at a frequency of from about 30 kHz to about 50 kHz.

17. The method of claim 15 further including the steps of providing an endoscope having a tubular channel, inserting the endoscope into a body opening, and inserting the endoscopic portion of the surgical instrument through the tubular channel of the endoscope.

18. The method of claim 15 wherein the endoscopic portion of the surgical instrument includes a tubular sheath and the ultrasonically vibratable element is slidably disposed within a bore of the tubular sheath.

19. The method of claim 18 wherein the step of closing the loop includes moving the vibratable element from a distal position wherein the loop is outside of the sheath and a proximal position wherein the loop is at least partially within the bore of the sheath.

20. The method of claim 15 wherein the surgical instrument includes an actuator which is movably connected to the housing and fixedly attached to the ultrasonically vibratable element, wherein movement of the actuator from a first position to a second position effects closing of the loop.

* * * * *